US00PP19274P2

(12) United States Plant Patent
Knauss

(10) Patent No.: US PP19,274 P2
(45) Date of Patent: Sep. 30, 2008

(54) ***CALATHEA* PLANT NAMED 'TWYCA0017 2'**

(50) Latin Name: *Calathea*
Varietal Denomination: TWYCA0017 2

(75) Inventor: Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/974,986

(22) Filed: Oct. 17, 2007

(51) Int. Cl.
*A01H 5/00* (2006.01)

(52) U.S. Cl. ..... Plt./375
(58) Field of Classification Search ..... Plt./375
See application file for complete search history.

*Primary Examiner*—Annette H Para
(74) *Attorney, Agent, or Firm*—Jondle & Associates, P.C.

(57) ABSTRACT

A new *Calathea* plant particularly distinguished by having a tall, upright plant habit with long-lasting, pink and green bracted inflorescences which are held high above the foliage, and large, elliptical leaves marked with broad metallic silver-green bands, is disclosed.

1 Drawing Sheet

Genus and species: *Calathea* hybrid
Variety denomination: 'TWYCA0017 2'.

BACKGROUND OF THE NEW PLANT

The present invention comprises a new and distinct cultivar of *calathea*, botanically known as *Calathea* hybrid and hereinafter referred to by the cultivar name 'TWYCA0017 2'. The new cultivar originated as a sport from a *Calathea* plant designated 'Mia' (U.S. Plant Pat. No. 16,425) in the fall of 2003 in Apopka, Fla.

A single plant selection was chosen for further evaluation and for asexual propagation in fall, 2003.

The new cultivar was first propagated in the fall of 2003 in Apopka, Fla. and has been asexually reproduced repeatedly by division and tissue culture over three generations. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Long-lasting, pink and green bracted inflorescences which are displayed above the patterned foliage; and 2. Elliptical leaves marked with a broad metallic silver-green band.

DESCRIPTION OF PHOTOGRAPH

This new *Calathea* plant is illustrated by the accompanying photograph which shows the overall plant habit including blooms and foliage of the plant; the colors shown are as true as can be reasonably obtained by conventional photographic procedures.

DESCRIPTION OF THE NEW CULTIVAR

The following detailed description sets forth the distinctive characteristics of 'TWYCA0017 2'. The data which define these characteristics were collected from asexual reproductions carried out in Apopka, Fla. The data were obtained in November 2006 from 14-month old plants from a 13 week old tissue culture derived line. The plants were grown in a greenhouse with fiberglass panel siding with inflated double poly roof with a modine heating, fan and pad cooling system. The average daily temperature was between 24° C. to 35° C. and the average nightly was between 18° C. and 24° C. Color readings were taken under natural light in the greenhouse. Color references are to The Royal Horticultural Society Colour Chart, 2001 edition.

DETAILED BOTANICAL DESCRIPTION OF THE NEW PLANT

Classification:
- *Family.*—Marantaceae.
- *Botanical name.*—*Calathea* hybrid.
- *Common name.*—*Calathea.*

Parentage:
- *Mutation parent.*—'Mia' *Calathea* hybrid (U.S. Plant Pat. No. 16,425).

Growth:
- *General.*—Tropical flowering potted plant; plant is suitable for use in shaded tropical landscapes and indoors.
- *Time to flower.*—14 months in a 25 cm pot starting from a 13-week old liner from tissue culture.
- *Appropriate container.*—15 cm to 20 cm pots; suitable for use in shaded tropical landscapes and indoors.

Plant description:
- *Life cycle.*—Herbaceous perennial.
- *Habit.*—Upright, wider than tall, inverted triangle, densely leafy; inflorescences upright and slightly above and among the foliage in the center of the plant; upright whorls of leaves arise from underground rhizome; rhizomaceous.
- *Vigor.*—Typical of *Calathea* commercial cultivars; vigrous.
- *Height* (*soil line to the top of the leaf canopy*).—44.0 cm to 52.0 cm.
- *Spread.*—62.0 cm to 75.0 cm.
- *Root color.*—RHS N199A to RHS N199B (Brown); tips RHS 145D.

*Temperature tolerances.*—High temperature of 105° F. to a low temperature of 40° F.

Branches:

*Branching habit.*—Basal branching, rhizomaceous.

*Number.*—18 basal branches.

*Length.*—Variable depending upon age of branch.

*Lateral branch diameter.*—1.0 cm to 1.5 cm.

Stems (Rhizomes):

*Description.*—Cylindrical, round in traverse section.

*Aspect.*—Horizontal, underground rhizome becoming upturned, vertical at tip.

*Strength.*—Thick, tough and fibrous.

*Internode length.*—0.8 cm to 2.8 cm.

*Color.*—RHS N170D tinged with RHS 147D.

Leaves:

*Arrangement.*—Alternate, simple, single, closely spaced in vertical ranks, rosette, with one to six leaves per lateral branch depending on age of the branch.

*Shape.*—Elliptical.

*Apex.*—Cuspidate.

*Base.*—Obtuse.

*Margin.*—Entire, wavy.

*Size.*—Length: 18.0 cm to 24.0 cm. Width: 12.0 cm to 16.0 cm.

*Color.*—Immature leaf: Upper surface: Leaf margin: Marked with a broad grey-green band of RHS 194B to RHS 194C variably marked with sparse dark-green flecks and streaks of RHS 147B along the leaf edge. Leaf center: RHS 147A to RHS 147B with faint green RHS 147B markings following the mid-rib. Lower surface: Upper surface pattern visible through the lower surface. Leaf margin: Marked with a broad band of RHS 191A variably marked with sparse flecks and streaks of RHS 191A to RHS 191B along with the leaf edge; edge of leaf trimmed with RHS 187A. Leaf center: RHS 191A to RHS 191B. Mature leaf: Upper surface: Leaf margin: Marked with a broad grey-green bank of RHS 190A to RHS 191B variably marked with sparse dark green flecks and streaks of RHS 147A along the leaf edge. Leaf center: Darker than, but closest to RHS 147A with RHS 147A to RHS 147B markings following the midrib. Lower surface: Upper surface pattern visible through the lower surface. Leaf margin: Marked with a broad band of RHS 191A to RHS 138C variably marked with sparse flecks and streaks of RHS 191A to RHS 189A along the leaf edge; edge of leaf trimmed with RHS 187A. Leaf center: RHS 189A to RHS 191A.

*Venation.*—Type: Pinnate. Color: Immature leaf Upper surface: Midrib (proximal): RHS 146B tinged with RHS 199A to RHS 199B. Midrib (distal): RHS 146B. Primary veins: RHS 147A to RHS 147B. Lower surface: Midrib (proximal): RHS 199A to RHS 199B. Midrib (distal): RHS 152D. Primary veins: RHS 147A to RHS 147B. Mature leaf Upper surface: Midrib: RHS 147B to RHS 146B. Primary veins: RHS 147A to RHS 147B. Lower surface: Midrib (proximal): RHS 146C tinged with RHS 152B. Midrib (distal): RHS 146C tinged with RHS 153C. Primary veins: RHS 147A.

*Texture.*—Upper surface: Glossy to shiny, concave between primary veins resulting in a slightly textured look. Lower surface: Matte, dull.

*Pubescence.*—Absent.

Petiole:

*Length (from basal attachment at rhizome to base of leaf).*—28.0 cm to 42.0 cm.

*Diameter.*—0.5 cm.

*Texture.*—Smooth with short, stiff, sparse pubescence.

*Color (both surfaces).*—RHS 146A to RHS 147A tinged with RHS 177A, with random streaks of RHS N186C.

*Petiole sheath.*—Encircles the rhizome and extends up the petiole to within 15.0 cm of the base of the leaf. Color: Outside: RHS 146A to RHS 147A tinged with RHS 177A with random streaks of RHS N186C. Inside: RHS 146B to RHS 146C; smooth, shiny.

*Cataphylls.*—Shape: Lanceolate. Apex: Acute. Base: Sessile, clasping rhizome. Length: 12.0 cm to 16.0 cm. Diameter (flattened): 3.0 cm. Color: Outside: RHS 147B to RHS 146B cast overall with RHS N186C to RHS N199B. Inside: Smooth, shiny RHS 195B to RHS 147C tinged proximally with RHS 182C. Texture: Outside covered with short, fine pubescence.

Geniculum:

*General.*—The orientation of the leaf to the petiole is variable, as the geniculum bends; during the night and early morning the geniculum is straight to somewhat curved, and the leaf is held nearly vertical above the foliage; during the day, the geniculum is curved, and the leaf is held outward.

*Length.*—2.5 cm.

*Diameter.*—0.6 cm.

*Color.*—RHS 147C tinged with RHS 199A to RHS 152B.

Flower bud:

*Size.*—Length: 1.5 cm. Diameter: 0.35 cm.

*Shape.*—Spindle shaped.

*Color.*—Translucent RHS 4D (Pale yellow). Faded buds: RHS 199C, becoming RHS 200A.

Inflorescence:

*Flowering season.*—Spring and fall.

*Arrangement.*—Inflorescence emerges from the center of the whorl of leaves; short branch spikes with two or three buds present under colourful bracts atop a tall upright spike.

*Inflorescence type.*—Tall, upright, terminally bracted spike; bracts arranged in closely spaced vertical ranks occupying the upper 4.0 cm to 6.0 cm of the spike; bracts remain for about 10 weeks.

*Inflorescence height.*—36.0 cm to 49.0 cm.

*Inflorescence width.*—8.0 cm from tip to tip of bracts across top of inflorescence.

*Number of flowers per inflorescence.*—12 to 14 buds.

*Quantity of flowers and buds per plant.*—12 spikes present; about 144 buds per plant.

*Fragrance.*—Absent.

*Flowering habit.*—Buds not observed to emerge or open fully.

Flowers:

*General.*—Persistent.

*Aspect.*—Outward.

*Shape.*—Tube like, staminodes and petals curve outward.

*Diameter.*—1.8 cm to 2.0 cm across face of the flower; tube diameter, 0.3 cm.

*Depth.*—3.3 cm.

*Longevity on the plant.*—1 day.

Petal:

*Appearance.*—Translucent, delicate, curved outward at the tips.

*Arrangement.*—Tube-like.

*Shape.*—Narrow, elliptic.

*Number.*—3.

*Margin.*—Entire.

*Apex.*—Acute.

*Base.*—Acute.

*Length.*—3.3 cm.

*Width.*—0.4 cm.

*Texture* (*Both surfaces*).—Smooth.

*Color when opening* (*Both surfaces*).—RHS 155C.

*Color when fully open* (*Both surfaces*).—RHS 155C.

*Color fading to.*—RHS 199C, becoming RHS 200A.

Staminodes:

*Appearance.*—Thin, crystalline, delicate.

*Arrangement.*—Tube-like, flared outward; reflexed at tips and along margins.

*Shape.*—Two are spatulate with emarginated tips; one short, reduced, linear, cupped at tip.

*Number.*—3.

*Margin.*—Entire.

*Length.*—3.3 cm; reduced staminode is 3.0 cm.

*Width.*—0.6 cm; reduced staminode is 0.3 cm.

*Texture* (*Both surfaces*).—Smooth.

*Color* (*Immature and mature* ).—Spatulate staminodes RHS 155C; reduced staminodes RHS 155C flushed with RHS N87D.

Sepal:

*Appearance.*—Translucent, pale white, crystalline.

*Arrangement.*—Tube-like.

*Shape.*—Narrow, elliptic to linear.

*Number.*—3.

*Margin.*—Entire.

*Apex.*—Acute.

*Base.*—Acute.

*Length.*—1.7 cm.

*Width.*—0.3 cm.

*Texture* (*Both surfaces*).—Smooth.

*Color* (*Immature — both surfaces*).—RHS 155C.

*Color* (*Mature — both surfaces*).—RHS 155C.

Peduncle:

*Length.*—31.0 cm to 49.0 cm.

*Diameter.*—0.4 cm.

*Angle.*—Straight upright.

*Strength.*—Tough, flexible.

*Texture.*—Smooth.

*Color.*—RHS 148A tinged with RHS 177A.

Bracts:

*General.*—Terminal bracts uppermost on raceme, subtended by fertile bracts with underlying branch spikes.

*Terminal bracts.*—Quantity: 10. Length: 4.2 cm. Width: 2.1 cm. Shape: Elliptic, flat or reflexed. Apex: Acute. Base: Acute. Margin: Entire, smooth. Color: Upper surface: Margin: RHS 186A to RHS 186B. Center distal: RHS 137B to RHS 138B tinged with RHS 144B. Center proximal: RHS 145B to RHS 145C. Lower surface: RHS 186A. Center distal: Tinged with RHS 187A to RHS. 187B Center proximal: RHS 145C. Texture: Upper surface: Smooth. Lower surface: Slightly rough.

*Fertile bracts.*—Quantity: 9. Length: 2.7 cm. Width: 3.4 cm. Shape: Broadly obovate. Apex: Emarginate. Base: Acute. Margin: Entire, smooth. Color: Upper surface: Margins: RHS 186B becoming RHS 186D near base. Center: RHS 145C to RHS 145D. Lower surface: Margins: RHS 186B becoming RHS 186D near base. Center: RHS 145C to RHS 145D. Texture: Upper surface: Smooth. Lower surface: Slightly rough.

Reproductive organs:

*Stamen.*—1.

*Anther.*—Shape: Lanceolate. Length: 0.1 cm. Width: 0.05 cm. Color: RHS 158D.

*Pollen.*—Amount: Sparse. Color: RHS 155D.

*Pistil.*—Number: 1. Length: 2.9 cm.

*Stigma.*—Shape: Elliptic, cupped. Color: RHS 155C.

*Style.*—Length: 2.9 cm. Width: 1.2 cm. Color: RHS 155C.

*Ovary.*—Inferior, 3-celled. Color: RHS 155C. Length: 0.2 cm. Width: 0.15 cm.

Fruit and seed set: Has not been observed.

Disease and Insect Resistance: Resistance and susceptibility is typical of the species.

COMPARISON WITH PARENTAL AND COMMERCIAL CULTIVARS

'TWYCA0017 2' differs from the mutation parent *Calathea* hybrid 'Mia' (U.S. Plant Pat. No. 16,425) in that 'TWYCA0017 2' has a green colored lower leaf surface, while 'Mia' has a dark-purple colored lower leaf surface.

'TWYCA0017 2' differs from the commercial variety *Calathea* named 'Eclipse' (U.S. Plant Pat. No. 9,621) in that 'TWYCA0017 2' has green colored lower leaf surface, while 'Eclipse' has a dark-purple colored lower leaf surface. 'TWYCA0017 2' has long lasting pink and green bracted inflorescences which are displayed above the foliage, while 'Eclipse' has green bracted inflorescences that are short scaped, inconspicuous and held among and below the foliage. 'TWYCA0017 2' is taller and has a more upright growth habit, while 'Eclipse' has a shorter, more spreading growth habit. Additionally, 'TWYCA0017 2' has large leaves, while 'Eclipse' has smaller leaves.

I claim:

1. A new and distinct cultivar of *Calathea* plant as shown and described herein.

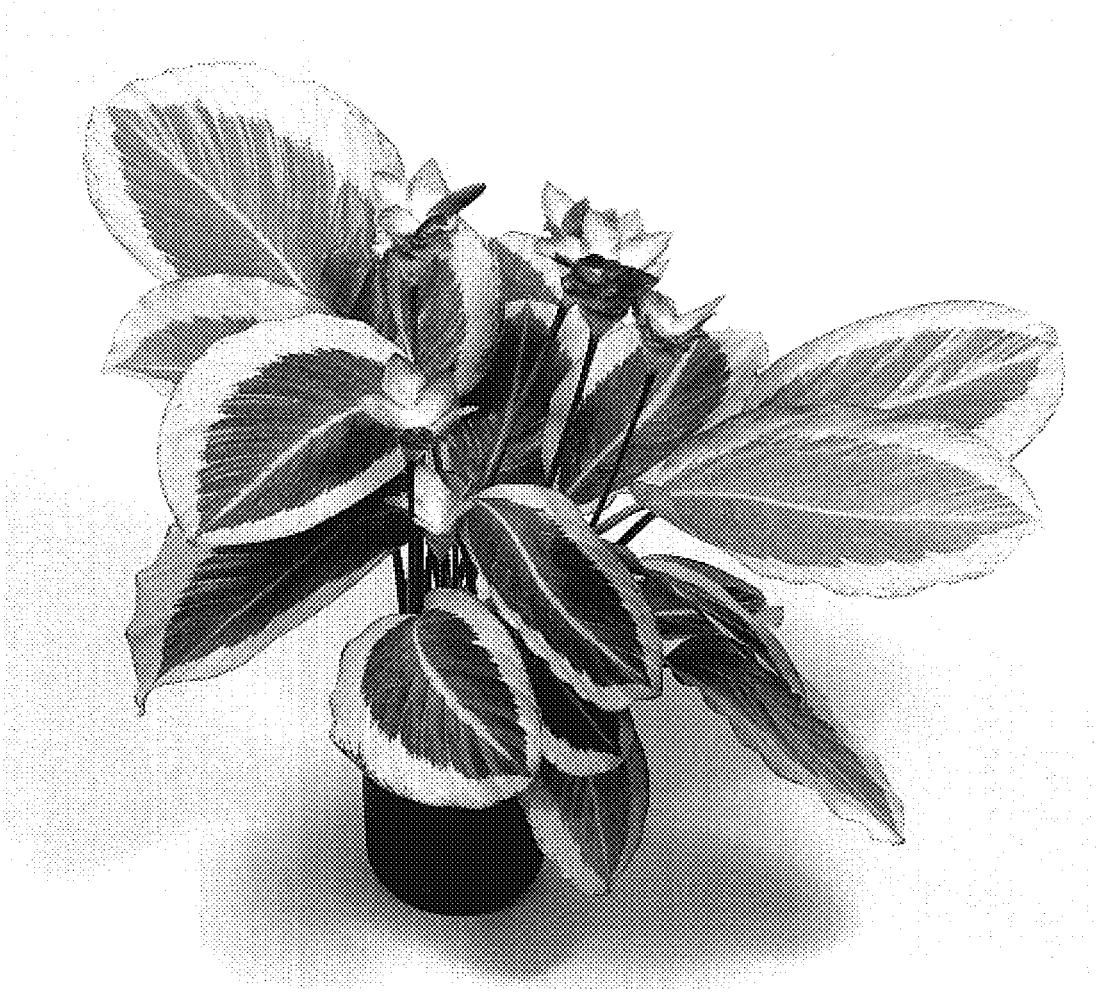

* * * * *